United States Patent [19]

Lund

[11] 4,245,043

[45] Jan. 13, 1981

[54] NEGATIVE CONTROL MEDIA DEVICE AND METHOD FOR MICROBIOLOGIC BIOCHEMICAL TESTS

[75] Inventor: Maryls E. Lund, Eden Prairie, Minn.

[73] Assignee: Minnesota Mining and Manufacturing Company, St. Paul, Minn.

[21] Appl. No.: 53,436

[22] Filed: Jun. 29, 1979

[51] Int. Cl.$^3$ .................... C12Q 1/20; C12M 1/20
[52] U.S. Cl. ........................ 435/33; 435/34; 435/36; 435/37; 435/38; 435/301
[58] Field of Search .............. 435/29, 30, 31, 32, 435/33, 34, 35, 36, 37, 38, 39, 40, 4, 301, 299, 300, 808, 810

[56] References Cited

U.S. PATENT DOCUMENTS

| | | | |
|---|---|---|---|
| 3,107,204 | 10/1963 | Brown et al. | 435/33 |
| 3,356,462 | 12/1967 | Cooke et al. | 422/102 |
| 3,441,383 | 4/1969 | Moore et al. | 422/102 |
| 3,713,985 | 1/1973 | Astle | 435/33 |
| 3,785,928 | 1/1974 | Kessler | 435/287 |
| 3,826,717 | 7/1974 | Gilbert et al. | 435/33 |
| 3,951,747 | 4/1976 | Yananton | 435/38 |
| 4,010,078 | 3/1977 | Taylor | 435/38 |
| 4,030,980 | 6/1977 | Beckford et al. | 435/33 |
| 4,077,845 | 3/1978 | Johnson | 435/33 |
| 4,154,795 | 5/1979 | Thorne | 422/99 |

*Primary Examiner*—Robert J. Warden
*Attorney, Agent, or Firm*—Cruzan Alexander; Donald M. Sell; Jennie L. Giese

[57] ABSTRACT

A microorganism identification test container comprises a tray member provided with a plurality of integrally formed open wells. A number of the wells are microorganism identification test wells having biochemical test media which in hydrated form permits growth of microorganisms with the generation of a volatile color-forming compound. Another number of wells are negative control wells corresponding to each of the test wells provided and including an inhibitor which in aqueous solution prevents color formation in the negative control wells from the volatile color-forming compound generated in the test wells. The wells are preferably disposed in a number of generally parallel rows or lines wherein one line or row contains a series of biochemical test media and an adjacent line or row contains the corresponding negative control medium for each test.

Biochemical test media used in the identification of microorganisms either contain an indicator or generate an indicator upon inoculation with microorganism, that responds to specific microorganism activity with a detectable change in color. Comparison between the negative control wells and the test wells, after inoculation and incubation of the microorganism, indicates the presence of a particular microorganism. Since many of the biochemical test media employ indicators that produce only subtle visually detectable changes in response to microorganism activity, the appearance of the negative control must remain essentially unchanged or subtle changes in the biochemical test wells will be difficult to perceive.

19 Claims, 2 Drawing Figures

NEGATIVE CONTROL MEDIA DEVICE AND METHOD FOR MICROBIOLOGIC BIOCHEMICAL TESTS

BACKGROUND OF THE INVENTION

1. Field of the Invention

The present invention relates to a device for use in the identification of microorganisms and more specifically to a means for eliminating the problem of false-positive reactions in negative control wells of microorganism identification test containers.

The large number of strains of highly pathogenic bacteria and their varying susceptibility to antibiotics has resulted in the development of techniques for microorganism identification and antibiotic susceptibility testing including the determination of the minimum inhibitory concentration of antibiotic, i.e., the lowest concentration of antibiotic which completely inhibits the growth of the organism. These techniques typically involve the use of test trays which comprise, for example, a one piece plastic shell containing a plurality of receptacles or incubation wells. The wells may be arranged in parallel rows such as described in U.S. Pat. Nos. 3,826,717 and 3,356,462, or in circular patterns such as described in U.S. Pat. No. 4,010,078.

During the antibiotic susceptibility test, the wells contain the microorganisms to be inhibited, nutrient broth and antibiotic. Typically before inoculation each of the antibiotic test wells contains a different concentration of antibiotic and each row of such wells contains a different antibiotic. Each of the wells is inoculated with a standard amount of microorganism. The contents of the wells are incubated for a period of time and are then examined to determine the minimum inhibitory concentration of the appropriate effective antibiotic, U.S. Pat. No. 3,826,717. Those wells which contain a sufficient concentration of a growth inhibiting antibiotic contain a clear solution, while those wells which contain an insufficient concentration of antibiotic or an ineffective growth inhibiting antibiotic have either a turbid solution or a small turbid area or dot surrounded by a clear solution, indicating growth of the microorganisms. Cross-contamination between test wells on the same plate is minimized by the use of barrier elements between rows of adjacent wells and by overlaying the openings of the wells with a cover or other sealing means.

During the microorganism identification test the wells contain the microorganism to be identified, nutrient broth and a biochemical indicator which changes in color in response to the appropriate microorganism, U.S. Pat. No. 4,010,078.

U.S. Pat. No. 3,107,204 discloses the use of an antibiotic test tray having wells containing fibrous discs. The discs contain dehydrated bacteriological media, a dye color indicator in accordance with bacterial growth or activity and various chemotherapeutic agents. The discs are arranged in pairs, each pair containing a high and a low concentration of the same antibacterial agent. Color changes are compared against a control to measure antibiotic activity, but not for identification of any particular active microorganism. The problem of cross-contamination of the materials in adjacent wells is recognized and overcome by the use of a sealing lid.

U.S. Pat. No. 4,010,078 provides a device for use in the identification of microorganisms comprising an open-topped multi-compartmented microorganism culture media receiving portion and a cover member. Several of the types of media employed contain an indicator which changes color in response to the growth of a particular microorganism. The use of a standard or negative control well is not discussed.

Heretofore the prior art has not provided an inexpensive microbial test tray which gives rapid results and not only provides antibiotic sensitivity information but further provides an accurate and reproducible means of microorganism identification through comparisons between negative control wells and biochemical test wells. An additional problem presented by microorganism identification is that many of the known biochemical tests involve only subtle color changes in the test media in response to microorganism growth. Determinations that these subtle color changes have occurred are difficult to make in a reliable manner. It is desired to improve the reliability of microorganism identifications based on subtle color changes in the biochemical test media.

SUMMARY OF THE INVENTION

The present invention provides a device and method which significantly improves the ability to detect the results of microorganism identification tests involving the detection of color changes in test media. The invention substantially reduces the possibility of an improper result in the identification of a microorganism due to failures to perceive subtle color changes in the test media.

The present invention provides increased reliability in microorganism identification by providing negative control wells which have an appearance identical to the test wells when the media in both types of wells are reconstituted with water and before the test wells are inoculated. The negative controls maintain the original color of the test media and provide a standard against which to compare the test media after inoculation and incubation with the microorganisms.

To be useful in a compact test tray, particularly one having several microorganism identification tests, the negative control wells must be closely adjacent to the corresponding test wells. The addition of a series of negative control wells lying adjacent to the test wells has been found to produce a problem of cross-contamination heretofore not experienced. Volatile products generated in the inoculated test wells can contaminate the negative control wells through vapor transport means and produce a false visible color change in the negative control wells. It is difficult to determine whether or not a true color change has occured in the test wells in response to microorganism activity without reference to a negative control which retains the standard color of the test well media.

The present invention does not eliminate the problem of cross-contamination of the negative controls, but does however, prevent color changes in the negative controls, by the inclusion of an inhibitor capable of preventing the volatile color forming compounds generated in the inoculated test wells from changing the color of the negative control media. The inhibitor is most conveniently provided as a buffer included in the negative control media at the time of filling and packaging the test tray. The present invention provides self-correcting negative controls, not requiring further operator manipulation, which enable the negative controls to retain the standard color of the test media.

The present invention provides negative control compositions which maintain their original color and are not affected by cross-contamination resulting from volatile products generated in the inoculated microorganism identification test wells. Thus, test results obtained through practice of the present invention are reproducible and accurate, i.e., free of false positive reactions in negative control wells.

The preferred embodiment of the present invention provides means wherein a multiplicity of tests employing many microorganism identification systems and many concentrations of numerous antibiotics may be performed in a single container in a rapid and efficient manner. The preferred embodiment is a tray containing microorganism identification test wells and negative control wells in addition to antibiotic test wells, with media in all the wells being furnished in a dry state ready for rehydration.

The present invention provides a device and method of identifying microorganisms which gives quick results and is readily employed in a simple and inexpensive way in hospitals, medical laboratories and doctor offices. In addition, since the present invention provides a more reliable and reproducible microorganism identification system, it significantly reduces the handling of potentially health-hazardous microorganisms by laboratory personnel.

DESCRIPTION OF THE PREFERRED EMBODIMENTS

Figure 1:
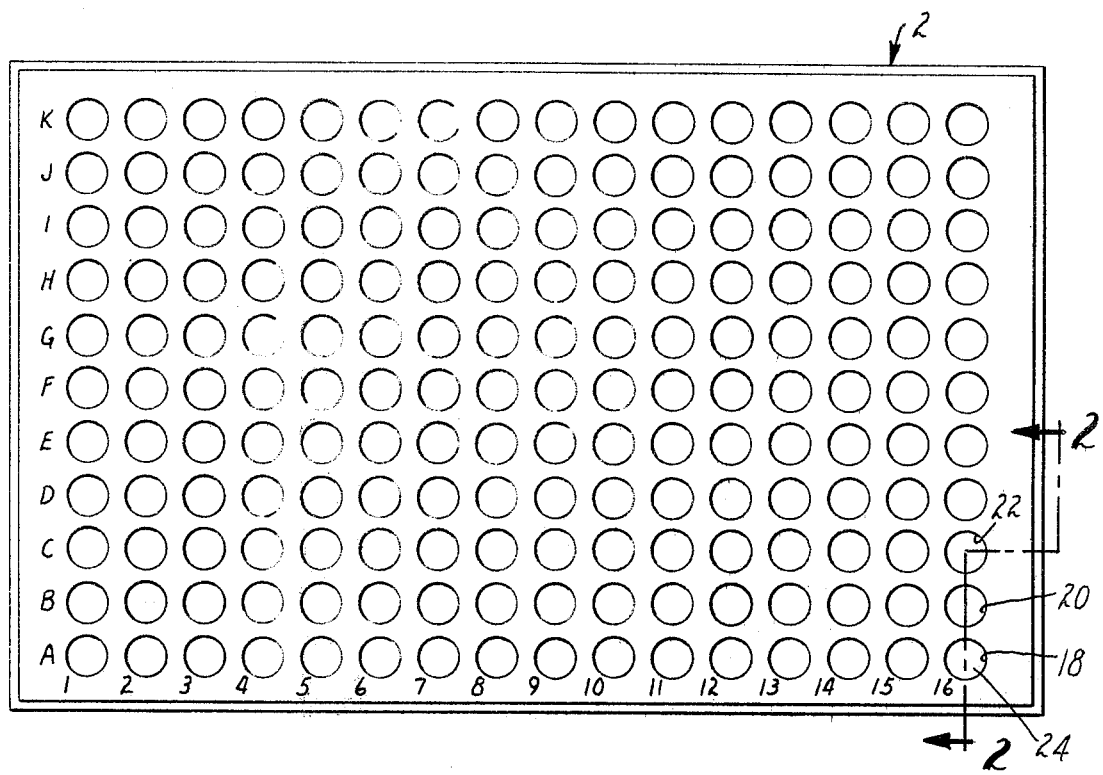
FIG. 1 is a partially schematic top plan view showing one embodiment of the combination antibiotic and microorganism test container of the present invention.
Figure 2:
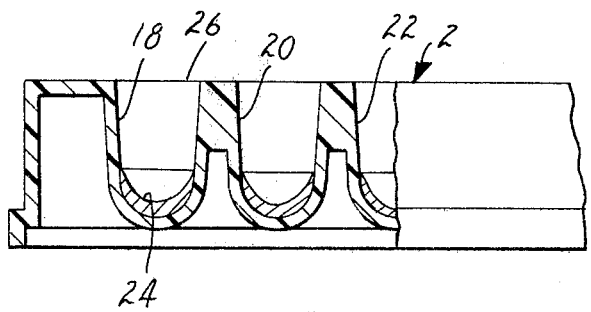
FIG. 2 is a side view of the antibiotic and microorganism test container of the present invention with a partial cross-section of the microorganism identification wells taken along 2—2 of FIG. 1.

Referring now more specifically to FIGS. 1 and 2, the embodiment of the invention there illustrated will be considered in greater detail. As is shown in FIG. 1, a tray member 2 is, in the form shown, of generally rectangular peripheral configuration. The tray member is preferably formed as a unitary article, as by molding. It is provided with a plurality of integrally formed upwardly open wells. In the form illustrated, the plate member 2 has sixteen vertical rows of wells and eleven horizontal lines of wells which are designated by the letters "A" through "K". The wells are downwardly directed cylinders having rounded bottoms.

The tray member 2 with wells may be made from a wide range of materials such as glass, plastic, or even a lightweight metal such as aluminum. It is generally preferred to mold these elements from a strong, liquid impermeable transparent plastic material. Among the materials particularly suited for such use are polyethylene, polypropylene, polystyrene, or the like. These materials not only possess the desired properties, but can also be economically manufactured into the desired shape by modern conventional plastic fabricating techniques. In addition, the use of such materials makes disposability after use economically feasible.

The preferred embodiment of tray member 2 is of generally rectangular configuration and has a length of 17.5 centimeters and a width of 11.0 centimeters. Wells in a given row are spaced ten millimeters apart and wells in adjacent rows are spaced nine millimeters apart.

Each well is of rounded-bottom cylindrical shape and has a depth of 10 millimeters, a diameter of 7 millimeters at the opening of the well and a curvature radius of 3 millimeters at the bottom, closed end of the well.

While the specific structure disclosed in detail herein has a generally rectangular periphery in plan and such geometry is preferred, the invention is not so limited and other external peripheral shapes may be employed while retaining the benefits of this invention. Also, while for purposes of illustration there have been shown the preferred rounded-bottom cylindrical wells, other configurations such as flat-bottom cylindrical wells or rectangular wells may be employed if desired.

Referring now to FIGS. 1 and 2, it is noted that each of the wells is filled with the appropriate substance (preferably by automatic filling means in a sterile environment) in such fashion that the upper surface 24 of the well contents will be disposed generally below the opening of the well 26. In the preferred embodiment the contents of the wells are air dried and must be reconstituted before use. It will be appreciated that while for purposes of convenience of description herein a tray member 2 having 16 rows each containing 11 wells is being shown, different numbers of rows containing different numbers of wells may be provided, depending upon the number of antibiotics and identification media used. Also, for a particular test, only those rows of wells which are to be employed in the test may be filled.

Referring to FIG. 1 in the preferred embodiment of the present invention, horizontal lines of wells "C" through "I" are antibiotic test wells (for example, well 22), each vertical row 1-16 containing a different antibiotic and each horizontal line C-I in each row containing a different concentration of the particular antibiotic. It is preferred that the wells of line "I" have the highest concentration of antibiotic and that the concentration be progressively decreased through line "C" which will contain the lowest concentration. Antibiotic control wells containing no antibiotic are also provided. Growth of microorganisms in the antibiotic control wells will confirm the fact that the microorganism will grow in the test system and will provide a basis for comparison with antibiotic test wells containing differing concentrations of antibiotic.

The effect of different types and concentrations of antibiotics on microorganism growth is normally not measured by a color change but rather is exhibited as a turbidity change when compared to adjacent clear or "no growth" wells having inhibitory concentrations of antibiotic.

Referring now to FIGS. 1 and 2, in the preferred embodiment of the present invention, horizontal lines of wells "A", "B", "J" and "K" are employed in microorganism identification tests. The wells in lines "A" and "K" are microorganism identification control wells (for example, well 18), also referred to as negative control wells, containing negative control media. The wells in lines "B" and "J" are microorganism identification test wells (for example, well 20), containing microorganism identification media. FIG. 2 illustrates that in the preferred embodiment negative control wells (e.g. 18) are placed in close proximity and adjacent to identification test wells (e.g. 20) which are adjacent to antibiotic test wells (e.g. 22).

Table I lists the type of media used in each microorganism identification test well (i.e. test media) of the preferred embodiment although different arrangements of the media and the use of additional or alternative media are not beyond the scope of the invention. Optimum concentrations may be determined for each ingredient in the various media listed in Table I, as is well known to the skilled artisan. Each of the test wells in lines "J" and "B" and therefore each of the corresponding negative controls in lines "A" and "K", contain a different medium depending on the microorganism to be identified, and each medium is capable of sustaining specific metabolic activity of a particular microorganism. Indicators are either added to the microorganism identification test media after inoculation with microorganism, as is known, or are generated in the test media by metabolism of the test media by the microorganism. The indicator produces a change in the color of the media in the test wells in response to microorganism metabolism. The activity of the organism under investigation is determined by a color change in the test media, as compared with the corresponding negative control.

TABLE I

| Row | Line | Medium | (Abbreviation) |
|---|---|---|---|
| 1 | J | Mueller-Hinton broth | (MH) |
| 2 | J | Lysine decarboxylase | (Lys) |
| 3 | J | Arginine dihydrolase | (Arg) |
| 4 | J | Ornithine decarboxylase | (Orn) |
| 5 | J | Sulfide detection | ($H_2S$) |
| 6 | J | Urease | (Ur) |
| 7 | J | Tryptophan deaminase | (TDA) |
| 8 | J | Indol | (I) |
| 9 | J | Voges-Proskauer | (VP) |
| 10 | J | Citrate utilization | (Cit) |
| 11 | J | DNAse detection | (DNA) |
| 12 | J | o-nitrophenyl-$\beta$-d-galactopyranoside | (ONPG) |
| 13 | J | Glucose fermentation | (Glu) |
| 14 | J | Arabinose | (Ara) |
| 15 | J | Inositol | (Ino) |
| 16 | J | Sorbitol | (Sor) |
| 1 | B | Mueller-Hinton broth | (MH) |
| 2 | B | Sucrose | (Suc) |
| 3 | B | Mannitol | (Man) |
| 4 | B | Rhamnose | (Rha) |
| 5 | B | Raffinose | (Raf) |
| 6 | B | Melibiose | (Mel) |
| 7 | B | Dulcitol | (Dul) |
| 8 | B | Adonitol | (Ado) |
| 9 | B | Malonate utilization | (Mal) |
| 10 | B | Esculin hydrolysis | (Esc) |
| 11 | B | Phosphodiesterase detection | (PDE) |
| 12 | B | MacConkey | (Mac) |
| 13 | B | Oxidation fermentation glucose | (OFG) |
| 14 | B | Oxidation-fermentation maltose | (OFM) |
| 15 | B | Oxidation-fermentation xylose | (OFX) |
| 16 | B | Pyocyanin | (Pyc) |

In the preferred embodiment it is essential that the original color of the test media contained in the test wells of lines "B" and "J" be maintained in the media of corresponding adjacent negative control wells in lines "A" and "K". When the organism to be tested is inoculated into the test wells of lines "B" and "J", a color change in the media contained in these wells will confirm the fact that the organism has metabolized in that particular test media. Negative control wells "A" and "K" provide a standard for comparison with the test wells (rows "B" and "J") in order to make possible the detection of even subtle color changes. If the original colors in the negative control wells are altered by cross-contamination, interpretations of microorganism identification tests may be erroneous.

Especially difficult problems have been observed in regards to the following negative control wells, line "A", row 11 (Phosphodiesterase medium), line "K", row 7 (Tryptophan deaminase medium), line "K", row 8 (Indol medium), line "K", row 9, (Voges-Proskauer medium), line "K", row 12 (o-nitrophenyl-$\beta$-d-galactopyranoside medium). The negative control media contained in these wells is clear and colorless and therefore is most susceptible to any cross-contamination by volatile color-forming compounds, resulting from the microorganism identification reactions occuring in adjacent test wells. Table II lists the cross-contaminating volatile color-forming compounds produced in the test wells.

TABLE II

| Test Well Row | Line | Negative Control Well Row | Line | Test Medium | Volatile Color-forming Compound |
|---|---|---|---|---|---|
| 11 | B | 11 | A | Phosphodiesterase | p-nitrophenol |
| 7 | J | 7 | K | Tryptophan deaminase | Indol |
| 8 | J | 8 | K | Indol | Indol |
| 9 | J | 9 | K | Voges-Proskauer | Acetoin |
| 12 | J | 12 | K | o-Nitrophenyl-$\beta$-d-galactopyranoside (ONPG) | o-nitrophenol |

In accordance with this invention, it has been found not only that color changes in negative control wells result from contamination by volatile color-forming compounds generated in the adjacent test wells upon inoculation but also that such undesirable color changes can be prevented by including in the negative control well media an inhibitor which in aqueous solution prevents color formation therein from the volatile color forming compound. The preferred inhibitor is a buffering system, i.e. one or more buffering compounds, capable of controlling the pH in the negative control wells.

p-Nitrophenol and o-nitrophenol are pH indicators which in acid solutions are colorless but which turn yellow when in the presence of alkaline solutions. Thus, negative control media which change their color when contaminated by o-nitrophenol or p-nitrophenol do so due to the color change of these pH indicators when exposed to a basic pH. On the other hand, negative control media which exhibit a color change when contaminated with indol or acetoin do so due to a chemical color-forming reaction between the negative control media and these cross-contaminants.

p-Nitrophenol and o-nitrophenol generated in phosphodiesterase and ONPG test medium after inoculation with microorganism may impart a yellow color to any medium having a basic pH. Therefore these volatile contaminants may change the color of even unrelated or noncorresponding negative control media having a basic pH. Negative control media lying adjacent to inoculated phosphodiesterase or ONPG test wells must either have a pH of 6.0 or below, or be buffered to such a pH in order to avoid color changes in the negative control media during microorganism identification testing.

Indol, generated in both the tryptophan deaminase test medium and the indol test medium will react with the indol negative control media to which is added the color forming coreactant p-dimethylaminobenzaldehyde.

In the preferred embodiment of the present invention the negative control wells having media corresponding to the Phosphodiesterase detection media, the Voges-Proskauer media and the o-nitrophenyl-$\beta$-d-galactopyranoside, must be maintained at a pH of 6 or below while microorganism identification reactions are occuring in adjacent phosphodiesterase and ONPG test wells in order to prevent color changes from occuring and thus false positive reactions. The preferred inhibitor for use with these media is monobasic potassium phosphate ($KH_2PO_4$).

The pH of the indol negative control media must be 9.8 or greater in order to prevent color changes from occuring in that negative control due to contamination from the adjacent corresponding inoculated indol test medium. The preferred inhibitor for the indol negative control is NaOH plus glycine.

After determining the identity of the volatile color forming contaminant, a suitable inhibitor useful in preventing color changes caused by that volatile contaminant in a given negative control can be selected by known laboratory procedures before the various media are introduced into the tray wells. For example, a series of runs under varying pH conditions can be used to select an appropriate buffering system so that no color change will occur in the negative controls.

In accordance with a preferred embodiment of the invention, the antibiotic test wells have antibiotic solutions introduced into them and the microorganism identification wells have the microorganism identification media, e.g. those of Table I, introduced into them. The contents of all wells are then air dried, and the device is packaged in a sealed, moisture proof wrapper or envelope for shipment to laboratory personnel. The antibiotic well contents are reconstituted before use with a nutrient broth. The microorganism test well contents are reconstituted with distilled water.

In order to provide a specific illustration of the use of the microorganism identification test system of this invention, four examples will be considered. These will illustrate the specific compositions of five particular microorganism identification test wells and the compositions of their corresponding negative control wells. The compositions of the negative control wells enable meaningful comparisons to be made between the test wells and the negative control wells due to retention in the negative control wells of the standard color of the corresponding microorganism identification test media. Because the purpose of the negative control is to provide a standard against which to compare color changes in the test medium, the negative control medium need contain only the buffering agent and those ingredients present in the test medium which add to the color of the test medium. The compositions listed illustrate the well contents prior to air drying.

EXAMPLE 1

The preparation of phosphodiesterase test medium and its negative control medium will be considered first. Phosphodiesterase test medium (PDE) is prepared by combining in a flask:

| | |
|---|---|
| *Peptone | 3.0 g |
| Thymidine-3'monophospho-p-nitrophenyl ester | 0.2 g |
| 0.1 M $Na_2HPO_4$ | 100 ml |

*Peptone is available under the tradename "Bacto-Peptone" from Difco Laboratories, Inc., Detroit, Michigan.

The solution is dissolved with stirring and, if necessary, the application of gentle heat ($\leq 50°$ C.). After the components are dissolved, the solution is filter sterilized through a 0.20 membrane filter. The filtrate is aseptically decanted into a sterile container for storage. The medium is stored, refrigerated and protected from light. The pH of the test medium is about $8.0 \pm 0.2$.

The corresponding phosphodiesterase negative control medium is prepared by combining in a flask:

| | |
|---|---|
| Peptone | 3.0 g |
| $KH_2PO_4$ | 10.0 g |
| Distilled water | 100 ml |

The solution is dissolved, filter sterilized and stored according to the procedure used for the phosphodiesterase reaction medium. The pH of the negative control medium is in the range of about 4.8 to 5.3, and in this example is about 5.0.

25 Microliters of the test medium and 25 microliters of control medium are introduced into separate adjacent wells of a test tray. The media in the wells are air dried. After rehydration with 100 microliters of sterile distilled water both the uninoculated test medium and the negative control medium are nearly colorless to pale straw in color. The pH of the rehydrated test medium is about $8.0 \pm 0.2$ and the pH of the rehydrated negative control medium is in the range of about 4.8 to 5.3, and in this example is about 5.0.

After the test wells are inoculated with *Serratia marcescens* and incubated overnight (16 to 18 hours) at 35° C. the test medium is yellow in color as compared to the uninoculated negative control medium which has remained nearly colorless throughout the test.

A negative control prepared according to the above formulation, but without the $KH_2PO_4$ exhibited a yellow color when tested under the same conditions. The pH of the unbuffered negative control was identical to that of the test medium, i.e. $8.0 \pm 0.2$. This change in the color of the unbuffered negative control is believed to be due to the fact that p-nitrophenol, a volatile contaminant generated in the adjacent inoculated test well, is an indicator which turns solutions not buffered to a pH of about 6.0 or below (such as the unbuffered negative control) yellow.

EXAMPLE 2 o-Nitrophenyl-$\beta$-D-galactopyranoside test medium (ONPG) is prepared by combining a flask:

| | |
|---|---|
| o-Nitrophenyl-$\beta$-D-galactopyranoside (ONPG) | 1.0 g |
| Isopropyl-$\beta$-D-thiogalactopyranoside (ITPG) | 0.08 g |
| *Peptone | 3.0 g |
| 0.1 M $Na_2HPO_4$ | 100 ml |

*Peptone is available under the tradename "Bacto-Peptone" from Difco Laboratories, Inc., Detroit, Michigan.

The ONPG is added by increments to the warmed ($\leq 50°$ C.) 0.1 M $Na_2HPO_4$ with continuous stirring. After the ONPG is completely dissolved the ITPG is added with continued heating and stirring. When the ITPG is dissolved the peptone is added to the solution with continued stirring. When the solution is completely dissolved it is filter sterilized through a 0.20$\mu$ membrane filter. The filtrate is aseptically decanted into a sterile container. The medium is stored under refrigeration and protected from light. The pH of the test medium is about $8.0 \pm 0.2$.

The corresponding ONPG negative control medium is prepared by combining in a flask:

| | |
|---|---|
| ONPG | 1.0 g |
| Peptone | 3.0 g |
| KH$_2$PO$_4$ | 10.0 g |
| Distilled water | 100 ml |

The solution is dissolved, filter sterilized and stored according to the procedure used for the ONPG test medium. The pH of the negative control medium is in the range of about 4.8 to 5.3, and in this example is about 5.0.

25 Microliters of the test medium and 25 microliters of the negative control medium are introduced into separate adjacent wells of a test tray, as in Example 1. The media in the wells are air dried. After rehydration with 100 microliters of sterile distilled water both the uninoculated test medium and the negative control medium are nearly colorless to straw in color. The pH of the rehydrated test medium is about 8.0±0.2 and the pH of the negative control medium is in the range of about 4.8 to 5.3, and in this example is about 5.0.

After the test wells are inoculated with *Klebsiella pneumoniae* and incubated overnight (16 to 18 hours) at 35° C. the test medium is yellow in color as compared to the uninoculated negative control which has remained nearly colorless throughout the test.

A negative control prepared according to the above formulation, but without the KH$_2$PO$_4$ buffering agent exhibited a yellow color when tested under the same conditions. The pH of the unbuffered negative control was identical to that of the test medium, i.e., 8.0±0.2. It is believed that the unbuffered negative control medium changes its original color because o-nitrophenol generated in the adjacent test wells after inoculation, (see Table II) turns solutions which it contaminates yellow if the pH of the solution is above about 6.0.

EXAMPLE 3

Voges-Proskauer test medium (VP) is prepared by combining in a flask:

| | |
|---|---|
| *Methyl red Voges Proskauer medium | 6.8 g |
| Creatine monohydrate | 3.0 g |
| Glucose | 3.0 g |
| Distilled water | 100 ml |

*Available under the tradename "MR-VP" from Difco Laboratories, Inc., Detroit, Michigan.

The solution is heated on a hot plate and stirred to dissolve completely. After the components are dissolved, the solution is covered and autoclaved at 121° C. for 10 minutes. The medium is stored under refrigeration. The pH of the test medium is about 6.7±0.2.

The corresponding negative control VP medium is prepared by combining in a flask:

| | |
|---|---|
| Methyl red Voges Proskauer medium | 6.8 g |
| Creatine monohydrate | 3.0 g |
| KH$_2$PO$_4$ | 12.0 g |
| Distilled water | 100 ml |

The solution is dissolved, autoclaved and stored according to the procedure used for the VP test medium. The pH of the negative control medium is about 5.8±0.2.

The VP test medium requires the addition of reagents, after inoculation with the microorganism in order to exhibit a color change in response to microorganism activity. Since the reagents may cause slight discoloration of the test medium, they should be added to both test and negative control media if an accurate color comparison is to be made.

25 Microliters of the test medium and 25 microliters of the negative control medium are introduced into separate adjacent wells of a test tray. The media in the wells are air dried. After rehydration with 100 microliters of sterile distilled water both the uninoculated test medium and the negative control medium are nearly colorless to straw in color. The pH of the rehydrated test medium is about 6.7±0.2. The pH of the rehydrated negative control is 5.8±0.2.

The test medium is inoculated with *Klebsiella pneumoniae* and incubated overnight (16 to 18 hours) at 35° C. 1 drop of 6% 2-naphthol and 1 drop 40% KOH (the reagents) are added to both the test medium and its corresponding negative control and the media are allowed to sit for 10-15 minutes. The addition of these reagents may impart an orange or rusty brown color to the negative controls. The test medium is cherry red in color as compared to uninoculated negative control which retains its original color.

A negative control prepared according to the above formulation, but without the KH$_2$PO$_4$ buffering agent exhibited a cherry red color when tested under the same conditions. The pH of the unbuffered negative control was identical to that of the test medium, i.e., 6.7±0.2. It is believed that the unbuffered negative control changes color due to a reaction between the volatile contaminant acetoin, generated in the inoculated adjacent test well (see Table II), and the negative control medium, which is not buffered to a pH of 6 or below; the reaction product being cherry red in color.

EXAMPLE 4

Tryptophan broth is prepared by combining in a flask:

| | |
|---|---|
| *Tryptone | 0.8 g |
| L-Tryptophan | 1.0 g |
| NaCl | 2.0 g |
| Polyvinylpyrrolidinone, Avg. MW = 10,000 | 1.6 g |
| 0.1 M Na$_2$HOP$_4$ | 2.0 ml |
| Distilled water | 98 ml |

*Sold under the tradename "Bacto-tryptone" by Difco Laboratories, Inc., Detroit, Michigan.

The solution is heated on a hot plate and stirred to dissolve completely. After the components are dissolved, the solution is covered and autoclaved at 121° C. for 15 minutes. The medium is stored under refrigeration. The tryptophan broth is used with appropriate reagents as both the indol and tryptophan deaminase test media. The pH of the tryptophan broth is 6.4±0.2.

The tryptophan deaminase microorganism identification test system will require a buffered negative control only when the negative control lies adjacent to test wells generating the volatile contaminants p-nitrophenol or o-nitrophenol, i.e., phophodiesterase detection medium and ONPG medium. Since these contaminants form yellow solutions when in the presence of basic media, the negative control must be buffered to a pH of 6.0 or below. In the preferred embodiment of the present invention the ONPG test well lies adjacent to the tryptophan deaminase test system and thus the tryptophan deaminase negative control must be buffered to a pH of 6.0 or below. Although inoculated tryptophan deaminase generates the volatile color-forming compound, indol, indol will not produce a color when in the presence of our tryptophan deaminase negative control medium. Indol will only produce a color change in negative control media containing p-dimethylaminobenzaldehyde, such as is the case in the indol negative control medium, see Example 5.

The corresponding tryptophan deaminase negative control medium is prepared by combining in a flask:

| Tryptone | 0.8 g |
| L-tryptophan | 1.0 g |
| NaCl | 2.0 g |
| KH$_2$PO$_4$ | 10.0 g |
| Distilled water | 100 ml |

The solution is dissolved, autoclaved and stored according to the procedure used for the tryptophan broth. The pH of the tryptophan deaminase negative control medium is in the range of about 4.3 to 5.2, and in this example is about 4.5.

For the tryptophan deaminase microorganism identification test 25 microliters of the tryptophan broth and 25 microliters of the tryptophan deaminase negative control medium are introduced into separate adjacent wells of the test tray of the preferred embodiment. 25 Microliters of the ONPG test medium of Example 2 are introduced into another adjacent well of the tray. The media in the wells are air dried. After rehydration with 100 microliters of sterile distilled water. The uninoculated broth, the negative control medium, and the uninoculated ONPG medium are nearly colorless to straw in color. The pH of the rehydrated broth is 6.7±0.2. The pH of the rehydrated negative control is in the range of about 4.3 to 5.2, and in this example is about 4.8.

The tryptophan deaminase test medium is inoculated with *Proteus rettgeri* and the adjacent ONPG test medium is inoculated with *Klebsiella pneumoniae*. The inoculated tray is incubated at 35° C. overnight (16 to 18 hours). The tryptophan deaminase test medium requires the addition of one drop of 10% ferric chloride after inoculation with the microorganism in order to exhibit a color change in response to microorganism activity. One drop of 10% ferric chloride is also added to the tryptophan deaminase negative control. The tryptophan deaminase test medium was dark brown in color as compared to its corresponding negative control which was orange. The inoculated ONPG test medium had turned a yellow color.

A tryptophan deaminase negative control was prepared according to the above formulation but without the KH$_2$PO$_4$ buffering agent. The pH of this unbuffered negative control was identical to that of the tryptophan deaminase test media, i.e., 6.7±0.2. When tested under the same conditions as the buffered negative control, that is, when placed adjacent to inoculated ONPG test medium, the negative control exhibited a yellow-orange color. It is believed that the unbuffered negative control changes color due to the fact that o-nitrophenol which is generated in the adjacent ONPG test well imparts a yellow color to solutions not buffered to a pH of about 6.0 or below.

EXAMPLE 5

Tryptophan broth prepared according to Example 4 is utilized also as the indol test medium. The pH of the indol test medium is 6.4±0.2.

The corresponding indol negative control medium is prepared by combining in a flask:

| *Tryptone | 0.8 g |
| Glycine | 9.0 g |
| NaCl | 2.0 g |
| 10N NaOH | 10 ml |
| Distilled water | 90 ml |

*Sold under the tradename "Bacto-tryptone" by Difco Laboratories, Inc., Detroit, Michigan.

The solution is dissolved, autoclaved, and stored according to the procedure used for the tryptophan broth, see Example 4. The pH of the indol negative control is 10.0±0.2.

25 Microliters of the tryptophan broth and 25 microliters of the negative control medium are introduced into separate adjacent wells of a test tray. The media in the wells are air dried. After rehydration with 100 microliters of sterile distilled water both the uninoculated test medium and the negative control medium are nearly colorless to straw in color. The pH of the rehydrated test medium is 6.7±0.2 and the pH of the rehydrated negative control medium is 10.0±0.2.

After the test medium is inoculated with *Escherichia coli* and incubated overnight (16 to 18 hours) at 35° C., 1-2 drops of Kovacs' reagent (alcoholic p-dimethylaminobenzaldehyde acidified with hydrochloric acid) is added to both the test medium and the corresponding negative control. The indol test medium requires the addition of Kovacs' reagent, after inoculation with the microorganism, in order for the test medium to exhibit a color change in response to microorganism activity. Kovacs' reagent must be added to both the test medium and the negative control since it will eventually turn the plastic tray rusty brown and thus may interfer with the identification of microorganism. After the addition of Kovacs' reagent the test medium turned red in color as compared to the negative control which was yellow as a result of the addition of Kovacs' reagent.

A negative control prepared according to the above formulation, but without the 10 N NaOH and glycine, the buffering agents, had a pH of about 6.7 and exhibited a red color when tested under the same conditions. It is believed that the unbuffered negative control medium changed color due to a reaction between the negative control medium at a pH of less than 9.8 and indol, a volatile contaminant generated in the corresponding indol test medium (see Table II), to produce a red colored product.

As illustrated by the Examples the formulations for the test media and their negative controls are four times the concentration of the media which is actually employed in the microorganism identification tests. If the media is to be used immediately, it should be diluted 1 to 4 with distilled water.

The concentrated formulations of the Examples work well if the media is to be dried and stored. Generally, as illustrated by the Examples, about 25 microliters of the concentrated microorganism identification media is dispensed into the wells of a test tray of the present invention. The media is allowed to air dry. Each well is then reconstituted by the addition of 100 microliters of sterile distilled water prior to inoculation.

Following inoculation, the organisms are allowed to incubate for about 16 to 18 hours. The media is then examined visually. If the original color is present, it may be deduced that the organism with which the medium was inoculated is a type which does not produce the metabolic product looked for in the particular medium. However, if the medium has changed to a different and characteristic color, it may be concluded that the organism inoculated is present, has grown, and has metabolized the substrate of interest in that particular medium.

I claim:

1. A device for use in the identification of microorganisms, comprising a unitary tray member having a plurality of integrally formed test wells, at least some of said wells serving as identification test wells for microorganisms and containing biochemical test media which in hydrated form permits growth of said microorganisms with the generation of a volatile color-forming compound, and corresponding negative control wells in close proximity to each of said test wells, said negative control wells containing negative control media including an inhibitor which in aqueous solution prevents color formation otherwise occuring therein from said volatile color forming compound, and wherein both said biochemical test media prior to inoculation with said microorganisms and said negative control media have the same color in hydrated form.

2. The device according to claim 1 wherein said inhibitor is a buffer.

3. A device according to claim 2 wherein said microorganism identification test wells contain said biochemical test media selected from the group consisting of phosphodiesterase medium, Voges-Proskauer medium, o-nitrophenyl-$\beta$-D-galactopyranoside medium, tryptophan deaminase medium and indol medium.

4. The device according to claim 3 wherein said buffer is selected from the group consisting of $KH_2PO_4$, and NaOH plus glycine.

5. The device according to claim 4 wherein at least one of said negative control wells contains phosphodiesterase negative control medium which comprises peptone buffered to a pH of about 4.8 to 5.3.

6. The device according to claim 4 wherein at least one of said negative control wells contain o-nitrophenyl-$\beta$-D-galactopyranoside negative control medium which comprises o-nitrophenyl-$\beta$-D-galactopyranoside and peptone buffered at a pH of about 4.8 to 5.3.

7. The device according to claim 4 wherein at least one of said negative control wells contains Voges-Proskauer negative control medium which comprises methyl red Voges Proskauer medium and creatine monohydate buffered to a pH of about 5.6 to 6.0.

8. The device according to claim 4 wherein at least one of said negative control wells contains tryptophan deaminase negative control medium which comprises tryptone, L-tryptophan, and NaCl buffered to a pH of about 4.3 to 5.2.

9. The device according to claim 4 wherein at least one of said negative control wells contains indol negative control medium which comprises tryptone and NaCl buffered to a pH of about 9.8 to 10.2.

10. A device according to claim 1 wherein each of said microorganism identification test wells contains a different biochemical test media, the color of which after inoculation with said microorganisms can be compared with the color of said media in said corresponding negative control wells to provide indicia for the accurate identification of said microorganisms.

11. A device according to claim 1 wherein said biochemical test media and said negative control media are present in said wells in dried form.

12. A device according to claim 1 wherein at least some of said wells serve as antibiotic test wells containing a predetermined concentration of an antibiotic, and antibiotic control wells, said control wells containing no antibiotic.

13. A device according to claim 12 wherein said biochemical test media, said negative control media and said antibiotic are present in dried form.

14. A device according to claim 12 wherein said wells are disposed in a number of generally parallel rows.

15. The device of claim 14 wherein:
(a) said antiobiotic test wells are disposed in several vertical rows, each of said vertical rows containing a different antibiotic with a different concentration of said antibiotic present in each of said test wells of said row; and
(b) said microorganism identification test wells and said negative control wells are disposed in pairs as horizontal lines of wells running perpendicular to said vertical rows of antibiotic test wells with each horizontal line of negative control wells lying adjacent to a horizontal line of said microorganism identification wells.

16. The device of claim 15 wherein:
(a) said vertical rows of antibiotic test wells number sixteen, each vertical row having seven antibiotic test wells, constituting seven horizontal lines of wells; and
(b) said pairs of horizontal lines of test wells and negative control wells number two with one of said pair of horizontal lines of rows running perpendicular and above said vertical antibiotic test rows and the other of said pairs running perpendicular and below said vertical antibiotic test rows; with said horizontal lines of rows of microorganism test wells and negative control wells constituting sixteen wells in each of said lines.

17. A method for the identification of microorganisms comprising:
(a) providing a unitary tray member having a plurality of integrally formed test wells, at least some said wells serving as microorganism identification test wells containing, in dried form, biochemical test media which in hydrated form permits growth of said microorganisms with the generation of a volatile color-forming compound and corresponding negative control wells in close proximity to each of said test wells, said negative control wells containing, in dried form, negative control media including a buffer which in aqueous solution prevents color formation therein from said volatile color forming compound, and wherein both said biochemical test media prior to inoculation with said microorganisms and said negative control media have the same color when in hydrated form;
(b) reconstituting the contents of said identification test wells and said negative control wells with water;
(c) inoculating said identification test wells with said microorganism;
(d) incubating said tray member; and
(e) comparing said identification test wells with said negative control wells to determine whether there has been a detectable change in said biochemical test media in said identification test wells, indicating activity of said microorganism.

18. A method for the identification of microorganisms according to claim 17 wherein an indicator capable of producing a color change in said biochemical test media, in response to microorganism growth, is added to said biochemical test media after inoculation with said microorganism.

19. The method of claim 17 including:

(a) providing some of said wells to serve as antibiotic test wells, containing in dried form, a predetermined concentration of an antibiotic, and antibiotic control wells containing no antibiotic;

(b) reconstituting the contents of said antibiotic test wells and said antibiotic control wells with a nutrient broth;

(c) inoculating said antibiotic test wells and said antibiotic control wells with said microorganism;

(d) incubating said antibiotic test wells and said antibiotic control wells;

(e) visually comparing said antibiotic test wells with said antibiotic control wells; and (f) determining the minimum concentration of antibiotic necessary to inhibit the growth of said microorganism.

* * * * *